United States Patent [19]
Fournier et al.

[11] 4,102,704
[45] Jul. 25, 1978

[54] PIGMENTARY COMPOSITIONS BASED ON ESTERS OF RESIN ACIDS AND AMINO-ALCOHOLS

[75] Inventors: Pierre Louis Edmond Fournier, Scotteville les Rouen; Jean Paul Mayer, Saint Etienne du Rouvray, both of France

[73] Assignee: Produits Chimiques Ugine Kuhlmann, Paris, France

[21] Appl. No.: 761,571

[22] Filed: Jan. 24, 1977

[30] Foreign Application Priority Data

Feb. 4, 1976 [FR] France .............................. 76 03040

[51] Int. Cl.² .............................................. C08K 5/23
[52] U.S. Cl. ........................... 106/288 Q; 106/308 N; 106/308 F
[58] Field of Search ............ 106/288 Q, 308 F, 308 N

[56] References Cited

U.S. PATENT DOCUMENTS

| 3,628,976 | 12/1971 | Stocher et al. | 106/308 F |
| 3,635,745 | 1/1972 | Rentel | 106/288 Q |
| 3,653,936 | 4/1972 | Wolf et al. | 106/288 Q |
| 3,841,889 | 10/1974 | Schrempp | 106/308 F |

Primary Examiner—Winston A. Douglas
Assistant Examiner—J. V. Howard
Attorney, Agent, or Firm—Beveridge, DeGrandi, Kline & Lunsford

[57] ABSTRACT

A pigmentary composition combining good rheological properties and high transparency with increased coloring power which comprises an intimate mixture of (a) an organic pigment and (b) one or more unmodified or modified resin acids esterified with an amino-alcohol; the intimate mixture is obtained by incorporating in the pigment in acid aqueous solution, a solution or dispersion of the ester, and then precipitating the ester by making the aqueous solution medium alkaline or by addition of an acid to form a salt insoluble in water.

11 Claims, No Drawings

PIGMENTARY COMPOSITIONS BASED ON ESTERS OF RESIN ACIDS AND AMINO-ALCOHOLS

The invention relates to a pigmentary composition containing an ester of a resin acid and an amino-alcohol, its method of preparation and its applications.

It is known to improve the transparency, the wettability, the dispersability and/or the rheology of the pigmentary compositions intended for printing inks by the incorporation of various adjuvants. Among these may be mentioned unmodified or modified resin acids.

By resin acids are meant more particularly those contained in colophony, such as, for example, abietic or primaric acids or their mixtures, or in a wider sense colophony itself.

The resin acids may be modified by disproportionation, hydrogenation or polymerisation, or by the action of maleic or fumaric acids; or by partial combination with polyalcohols such as glycerine, pentaerythritol or ethylene glycol so as to obtain acid esters; or by reaction with phenolformaldehyde condensation products or with glycerol and phthalic anhydride, so as to obtain acid resins, . . . .

Other known adjuvants are the metal salts of resin, such as calcium, barium, or zirconium resinates, or the organic amines described for example in French Pat. No. 1,538,270 filed on Sept. 29, 1967, and the Belgian Pat. No. 660,978 filed on July 1, 1965, or small quantities of products which improve the wetting such as the oleic ester of triethanolamine.

However, the improvements obtained due to these various known adjuvants are limited by the loss of colouristic intensity caused by their addition.

The object of the present invention is to remove this drawback from the state of the art, and the invention relates to a pigmentary composition combining good rheological properties and a high transparency with a remarkable colouristic power taking into account the high content of colourless substance.

Another object of the invention is to realize an excellent coating of the pigment in a simple way directly in aqueous medium, without being compelled to have recourse to complicated (and expensive) treatments such as "flushing" or treatment in solvent medium.

The new pigmentary composition comprises an intimate mixture of an organic pigment with an ester of an amino-alcohol and one or more resin acids which may be modified or unmodified.

The chemical constitution of the organic pigment contained in the new composition is not defined in a limited manner and numerous classes of pigments are suitable. However, azo pigments, and especially the yellow pigments of diarylides have proved specially advantageous. By these are meant pigments derived from a tetrazotisable base and a coupling component of the acetylacetanilide group.

The unexpected feature of the considerable increase in the colouring power will appear more clearly during the explanations and Examples which follow.

The amino-alcohol and the acid or acids entering into the constitution of the ester may be pure products, but are preferably technical products which may contain impurities.

The amino-alcohol is generally a tertiary amine such as triethanolamine. The latter may contain small amounts of mono- or di-ethanolamine, which may go up to 10% by weight, and the condensation products which constitute the ester may then contain small quantities of amide.

According to the invention, taking triethanolamine as the aminoalcohol, the ester may be considered as a statistic mixture formed from products in which 1, 2 or 3 alcoholic functions of the said triethanolamine are esterified. In most cases, statistically speaking, one or 2 of these 3 functions are esterified, the ester most often comprising free remaining alcoholic functions. This ester is called "unmixed ester".

According to the invention the ester may be a mixed ester of one or more unmodified or modified resin acids and one or more other mono- or di-carboxylic or sulphonic acids having from 2 to 25 carbon atoms. This ester is called "mixed ester".

The said mono- or di-carboxylic acids are preferably aliphatic or aromatic, for example, acetic, propionic, heptanoic, dodecylic, stearic, oleic, benzoic, phthalic, or succinic acids.

Of the sulphonic acids may be mentioned benzene-, toluene-, xylene- or naphthalene- mono- or possibly disulphonic acids.

The ester may be present in the new composition in the form of a free amine. It may also be present in the form of the water-insoluble salt of a mono- or di-carboxylic or sulphonic acid having from 2 to 25 carbon acids or of an unmodified or modified resin acid, defined above.

The other acid used for obtaining the mixed ester may be the same as the acid used for forming a water-insoluble salt of the ester, or it may be different.

The quantity of acid used for forming the said water-insoluble salt is preferably at least stoechiometric, and generally at most 1,2 times the stoechiometric quantity.

The acids listed above are preferably mono-carboxylic acids having from 6 to 18 carbon atoms and belonging to the aliphatic series, or dicarboxylic acids such as phtalic or succinic acids.

The precipitation of the ester by means of an acid as described above is realised at a pH comprised between 4 and 10 and preferably between 4, 5 and 8.

The precipitation of the ester by means of alcalinisation is performed at a pH of at least 11.

The new composition also contains one or more of the adjuvants mentioned above as known, especially one or more unmodified or modified resin acids.

The new composition generally contains from 0.5 to 60% by weight of the ester and more particularly from 10 to 40% by weight.

The condensation reaction providing the ester may be effected in the absence or presence of a solvent or a diluent and/or of a catalyst, by transposing in the said reaction the methods already known for the preparation of esters of fatty acids and hydroxylated tertiary amines described in French Pat. No. 669,517, German Pat. Nos. 546,406 and 578,570, and the Revue Francaise des Corps Gras 1961, No. 3, page 140 (M. C. Demarcq). In general the condensation is carried out at a temperature of 200°-220° C, the reaction being continued while stirring until the water from the condensation is eliminated, the use of vacuum conditions being preferable.

Preferably the intimate mixture constituting the new pigmentary composition is obtained by incorporating in the pigment, which is in the form of an acid aqueous suspension, a solution of the ester in a solvent miscible with water, or a dispersion of the ester in acidulated water, then precipitating the said ester by making the water alkaline or by addition of a mono- or di-carboxylic acid having from 2 to 25 carbon atoms or an unmodified or modified resin acid, this addition resulting in the formation of a salt insoluble in water.

The pigmentary composition is generally separated by filtration, and is then washed until mineral salts are eliminated and dried, preferably at a temperature below 100° C.

The ester and pigment are preferably brought together with good stirring, at a pH less than 6, which according to the observation of the applicant, favours the dispersion of the ester. The ester and the pigment may be mixed before or during the coupling process, but it is generally preferred to be effected after the latter, the pigment being able to have been previously washed and put in aqueous suspension.

The solvent miscible with water used to dissolve the ester is mostly an alcohol such as methanol, propanol or more especially ethanol, but it is also possible to take acetone, cellosolves, the mono- and di-ethylethers of diethylene glycol, this list not being restricted: the choice of solvent is, of course, a function of the constitution of the ester.

It is also possible, although not preferred, to effect a method of incorporation which comprises flushing the pigment in a solution of the ester in a solvent, or the addition of the ester to a suspension of the pigment in a solvent followed by the elimination of this solvent.

The new pigmentary composition may be used for all the usual functions of pigments, specially the pigments consisting of azo compounds of diarylides, but is applied with particular advantage to the colouration of printing inks, for which there is required of these pigments the qualities of transparency and high colouring power, especially fatty inks intended for typographic and offset printing, liquid inks based on metal resinates or olefine resins (heliographic printing), liquid inks for packings or crates based on polar solvents.

The following Examples in which the parts are parts by weight illustrate the invention without thereby limiting its scope.

EXAMPLE A 300 parts of disproportionate colophony and 150 parts of triethanolamine are introduced into a distillation flask preferably provided with a stirrer. It is slowly heated under vacuum (about 20 mm Hg) while stirring when the mixture is sufficiently fluid. Heating is therefore effected up to 200°-220° C for about 3 hours: 18 to 20 parts of water are collected in the distillate.

About 425 parts of a product are obtained by cooling, which is readily soluble in alcohol, insoluble in water, but dispersible in water containing a little acetic acid.

EXAMPLE B 300 parts of disproportionate colophony and 150 parts of triethanolamine are condensed as in Example A, and then 130 parts of heptanoic acid are added and the mixture is again heated under vacuum to 200°-220° C while collecting 18 to 20 parts of water .

On cooling, about 530 parts of a product insoluble in water and soluble in alcohol are obtained.

EXAMPLE 1

Solution (1). A solution of tetrazotised 3,3'-dicholorobenzidine is prepared in the usual way from 63, 25 parts of 3,3'-dichlorobenzidine base, 300 parts of 5N hydrochloric acid and 36.2 parts of sodium nitrite in 1000 l parts of water at 0°.

Solution (2). 109 parts of acetylacetometaxylidide are dissolved with 40 parts of sodium hydroxide in 1000 parts of water.

Solution (3). 8.6 parts of a disproportionate colophony are dissolved with 1.6 parts of sodium hydroxide and 500 parts of water. 17.5 parts of sodium acetate are dissolved in 500 parts of water in a coupling vessel and the pH is adjusted to 4.5 with about 12 parts of acetic acid.

5% of solution (2) is added, then the whole of the 3 solutions (1), (2) and (3), in about an hour, et a temperature of 30° C, while verifying the absence of free tetrazo compound in the formation.

After the coupling, 65.6 parts of the product of Example A in alcoholic solution are added, in mixture is stirred for 15 minutes, and then 21.8 parts of heptanoic acid in the form of an aqueous solution of its sodium salt are added, the mixture is made alkaline to pH 7.0-7.5 with caustic soda and heated 1 hour at 80° C. It is filtered and the solid washed and dried at 60° C. About 230 parts of a yellow powder are obtained, which when incorporated by grinding on a tricylindrical machine in a conventional binder for fatty ink gives an ink of intensity and transparency superior to those abtained with the base pigment alone and of similar rheological behaviour.

EXAMPLE 2

A suspension of the pigment 3,3'-dichlorobenzidine→acetylacetometaxylidide is prepared as in Example 1.

After the coupling, 69 parts of the product of Example B in the form of an alcoholic solution are added to the formation. It is stirred for 15 minutes and 18.25 parts of heptanoic acid in the form of a 10% aqueous solution of its sodium salt are added. The mixture is made alkaline to pH 7.0-7.5 with soda and heated for 1 hour at 80° C. The solid is filtered off, washed and dried at 60° C. 235 parts of a yellow powder are obtained, which when incorporated by grinding on a three cylinder machine in a conventional binder for fatty ink gives an ink of intensity comparable with that obtained in Example 1, and of transparency slightly inferior but of better rheological behaviour.

EXAMPLE 3

The solutions of Example 1 are prepared but replacing in solution (2) the actylacetometaxylidide by 95.5 parts of acetylacetanilide, and using for the solution (3) 7.9 parts of disproportionate colophony and 1.12 parts of sodium hydroxide and 500 parts of water.

The coupling is effected at the ambient temperature in the same conditions as previously. The product is then heated to 60° C, the solid filtered off and washed with water.

The paste is taken up in 1500 parts of water, while stirring vigorously; 78.6 parts of the product of Example A are added in the form of a solution in alcohol, the pH is adjusted to 5 with acetic acid and it is stirred for 30 minutes. Then the medium is made alkaline to a pH of 12 with a sufficient quantity of soda, and it is heated for 1 hour at 60° C. The solid is filtered off, washed and dried at 60°0 C. 215 parts of a pigmentary composition are obtained which, incorporated by grinding with a conventional binder for helio-edition ink based on metal resinates, gives an ink of intensity greater than that obtained with the untreated pigment.

EXAMPLE 4

A paste containing the pigment 3,3'-dichlorobenzidine→acetylacetanilide is prepared as in Example 3. The paste is taken up with 1500 parts of water, with vigorous stirring, 53.7 parts of the product of Example A in the form of a solution in ethanol are added, the pH is adjusted to 5 with acetic acid and stirring is effected for 30 minutes.

Then 13.7 parts of lauric acid in the form of a 10% aqueous solution of its sodium salt are added, then the pH is raised to 7.5 with a sufficient amount of soda and it is heated at 60° C for 1 hour. The solid is filtered off, washed and dried at 60° C. About 215 parts of a pigmentary composition are obtained of which the properties are similar to those of Example 3.

EXAMPLE 5

A solution of tetrazotised 3,3'-dichlorobenzidine is prepared as previously, from 63.25 parts of 3,3'-dichlorobenzidine in 1000 parts of water at 0° C.

On the other hand, 142 parts of 2'5'-dimethoxy-4'-chloro-acetylacetanilide are dissolved with 21 parts of sodium hydroxide in 1000 parts of water. This solution is run into 750 parts of iced water containing 115 parts of 5N hydrochloric acid, with vigorous stirring, then 145 parts of sodium acetate are added and it is heated to 60° C.

Then the tetrazo solution is run in slowly on verifying the absence of this compound in the formation.

After the coupling, the product is heated at 95° C for 1 hour, filtered and the solid washed. The paste is taken up with 2000 parts of water with brisk stirring, 102.2 parts of the product of Example A are added. The pH is adjusted to 5 with acetic acid and stirring is effected for 30 minutes. The medium is made alkaline at pH 12 with a sufficient amount of soda and it is heated for 1 hour at 85° C. The solid is filtered off, washed and dried at 60° C. About 282 parts are obtained of a pigmentary composition which, when incorporated by grinding with a binder for helio ink for packings based on nitrocellulose, gives an ink of intensity similar to that obtained with an untreated product.

The calculation hereafter, which may also be applied to Examples 1 to 4 and 6 of the present application, enables the gain in colouring power obtained due to the invention to be calculated.

In the present Example 5, the 282 parts of pigmentary composition obtained contain 282 − 102.2 = 179.8 parts of pure pigment, and enable an ink to be obtained of the same weight and or intensity similar to that obtained with taking 282 parts of pure pigment. In other words and on reducing the proportions to 100 parts of pure pigment, 64 parts of pigment in the pigmentary composition have the same intensity (colouring power) as 100 parts of free pure pigment.

EXAMPLE 6

As in Example 5 a paste is prepared containing the pigment 3,3'-dichlorobenzidine→2'5'-dimethoxy-4'-chloro-acetylacetanilide. The paste is taken up in 2000 parts of water with brisk stirring. 85.9 parts of the product of Example A in alcoholic solution are added. The pH is adjusted to 5 with acetic acid and stirring is continued for 30 minutes.

16.1 parts of phthalic anhydride are added in the form of a solution of 10% sodium phthalate; the pH is adjusted to 7.0-7.5 with soda and it is heated for 1 hour at 85° C. It is filtered and the solid washed and dried at 60° C.

About 285 parts of a pigmentary composition of properties similar to that of Example 5 are obtained.

What we claim is:

1. A pigmentary composition comprising an intimate mixture of (a) an organic pigment and (b) one or more unmodified or modified resin acids esterified with an aminoalcohol, wherein the intimate mixture constituting the new pigmentary composition is obtained by incorporating in the pigment, which is in the form of an acid aqueous suspension, a solution of the ester in a solvent miscible with water, or a dispersion of the ester in acidulated water, then precipitating the said ester by making the aqueous reaction medium alkaline or by addition of a monocarboxylic acid having from 2 to 25 carbon atoms or dicarboxylic acid or an unmodified or modified resin acid, this addition resulting in the formation of a salt insoluble in water.

2. A pigmentary composition according to claim 1, in which the pigment is a yellow azo diarylides pigment.

3. A composition according to claim 2, in which the ester is a mixed ester of one or more unmodified or modified resin acids and one or more other mono-carboxylic or sulphonic acids having from 2 to 25 carbon atoms or dicarboxylic acid.

4. A composition according to claim 2, in which the ester is in the form of a salt insoluble in water of a monocarboxylic acid or sulphonic acid having from 2 to 25 carbon atoms or dicarboxylic acid or an unmodified or modified resin acid.

5. A composition according to claim 2, which contains one or more adjuvants known for the pigmentary compositions intended for printing inks.

6. A composition according to claim 2, in which its content of ester is from 0.5 to 60% by weight.

7. A pigmentary composition according to claim 2, in which the pigment and the ester are brought together at a pH less than 6, the ester being introduced as a solution in a solvent miscible in water.

8. A pigmentary composition according to claim 7, in which the precipitation of the ester is performed by adding to it a mono-carboxylic aliphatic acid having from 6 to 18 carbon atoms or phtalic or succinic acid, the pH being comprised between 4 and 10, the ester used being unmixed ester.

9. A pigmentary composition according to claim 7, in which the precipitation of the ester is performed by making the aqueous reaction medium alkaline to a pH of at least 11, the ester used being unmixed ester.

10. A pigmentary composition according to claim 7, in which the precipitation of the ester is performed by adding to it a mono-caboxylic aliphatic acid having from 6 to 18 carbon atoms or phtalic or succinic acid, the pH being comprised between 4 and 10, the ester used being mixed ester, the other acid used for the esterification being a mono-carboxylic aliphatic acid having from 6 to 18 carbon atoms.

11. A pigmentary composition according to claim 1 in which the amino-alcohol is triethanolamine.

* * * * *